United States Patent
Lattner et al.

(10) Patent No.: US 6,618,627 B2
(45) Date of Patent: *Sep. 9, 2003

(54) INTRAORAL ELECTROMUSCULAR STIMULATING DEVICE AND METHOD

(75) Inventors: Stefanie Lattner, Gibsonia, PA (US); Eric W. Starr, Allison Park, PA (US); Eugene N. Scarberry, Trafford, PA (US); Douglas M. Mechlenburg, Pittsburgh, PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/817,434

(22) Filed: Mar. 26, 2001

(65) Prior Publication Data

US 2003/0069626 A1 Apr. 10, 2003

Related U.S. Application Data

(63) Continuation of application No. 09/436,857, filed on Nov. 9, 1999, now Pat. No. 6,212,435.
(60) Provisional application No. 60/108,408, filed on Nov. 13, 1998.

(51) Int. Cl.$^7$ .................................................. A61N 1/05
(52) U.S. Cl. ........................................ 607/134; 607/42
(58) Field of Search .............................. 607/42, 58, 63, 607/134; 600/529; 128/848

(56) References Cited

U.S. PATENT DOCUMENTS

| | | |
|---|---|---|
| 3,480,010 A | 11/1969 | Crossley |
| 4,153,060 A | 5/1979 | Korostoff et al. |
| 4,334,542 A | 6/1982 | Takinishi et al. |
| 4,365,636 A | 12/1982 | Barker |
| 4,433,693 A | 2/1984 | Hochstein |
| 4,519,400 A | 5/1985 | Brenman et al. |
| 4,580,575 A | 4/1986 | Birnbaum et al. |
| 4,637,405 A | 1/1987 | Brenman et al. |
| 4,669,459 A | 6/1987 | Spiewak et al. |
| 4,715,367 A | 12/1987 | Crossley |

(List continued on next page.)

FOREIGN PATENT DOCUMENTS

| | | |
|---|---|---|
| EP | 0 597 891 B1 | 3/1992 |
| EP | 0 494 787 B1 | 9/1992 |
| EP | 0 702 977 A2 | 9/1995 |
| SU | 1424-792 A | 5/1986 |
| SU | 1553140 A1 | 3/1990 |

OTHER PUBLICATIONS

Guiuseppe Sant' Ambrogio et al., "Sensory Information from the Upper Airway: Role in the Control of Breathing," Respiration Physiology, vol., 102, 1995, pp. 1–16.

(List continued on next page.)

Primary Examiner—George R. Evanisko
(74) Attorney, Agent, or Firm—Michael W. Haas

(57) ABSTRACT

An intraoral electromuscular stimulation device and method to treat a breathing disorder. The stimulation device includes a first electrode, a first support member that maintains the first electrode in a sublingual location posterior to a frenulum and proximate to one of a first molar, a second molar and a third molar of a patient. A second electrode is maintained in a sublingual position posterior relative to the first electrode by a second support member. A further embodiment of the stimulation device includes a sensor that detects a respiratory parameter of a patient and outputs a signal indicative thereof. A control unit receives the signal from the sensor, distinguishes between inspiration and expiration, and initiates an electrical stimulation at a stimulation time prior to onset of inspiration and continues stimulation through a portion of inspiration at a level sufficient to induce muscle contraction without pain.

14 Claims, 8 Drawing Sheets

U.S. PATENT DOCUMENTS

| | | | |
|---|---|---|---|
| 4,788,533 A | 11/1988 | Mequignon | |
| 4,830,008 A | 5/1989 | Meer | |
| 4,907,602 A | 3/1990 | Sanders | |
| 5,123,425 A | 6/1992 | Shannon, Jr. et al. | |
| 5,133,354 A | 7/1992 | Kallok | |
| 5,146,918 A | 9/1992 | Kallok et al. | |
| 5,158,080 A | 10/1992 | Kallok | |
| 5,174,287 A | 12/1992 | Kallok et al. | |
| 5,178,156 A | 1/1993 | Takishima et al. | |
| 5,190,053 A | 3/1993 | Meer | |
| 5,211,173 A | 5/1993 | Kallok et al. | |
| 5,215,082 A | 6/1993 | Kallok et al. | |
| 5,233,983 A | 8/1993 | Markowitz | |
| 5,265,624 A | 11/1993 | Bowman | |
| 5,277,193 A | 1/1994 | Takishima et al. | |
| 5,281,219 A | 1/1994 | Kallok | |
| 5,284,161 A | 2/1994 | Karell | |
| 5,330,527 A | 7/1994 | Montecalvo et al. | |
| 5,483,969 A | 1/1996 | Testerman et al. | |
| 5,485,851 A | 1/1996 | Erickson | |
| 5,522,862 A | 6/1996 | Testerman et al. | |
| 5,540,731 A | 7/1996 | Testerman | |
| 5,540,732 A | 7/1996 | Testerman | |
| 5,540,733 A | 7/1996 | Testerman et al. | |
| 5,546,952 A | 8/1996 | Erickson | |
| 5,549,655 A | 8/1996 | Erickson | |
| 5,591,216 A | 1/1997 | Testerman et al. | |
| 5,678,535 A | 10/1997 | DiMarco | |
| 5,792,040 A | 8/1998 | Koeneman et al. | |
| 5,792,067 A | 8/1998 | Karell | |
| 6,212,435 B1 * | 4/2001 | Lattner et al. | 607/134 |

OTHER PUBLICATIONS

American Review of Respiratory Disease, "Arousal: The Forgotten Response to Respiratory Stimuli," vol. 118, 1978, pp. 807–809.

American Sleep Disorders Association Task Force, "The Chicago Criteria for Measurements, Definitions, and Severity Ratings of Sleep Related Breathing Disorders in Adults," 1997, pp. S1–S19.

Michael J. Decker et al., "Functional Electrical Stimulation and Respiration During Sleep," J. Appl. Physiol., 1993, pp. 1053–1061.

Lee C. Edmomds et al., "The Effects of Transcutaneous Electrical Stimulation During Wakefulness and Sleep in Patients with Obstructive Sleep Apnea," Am Rev Respir Dis., 1992, pp. 1030–1036.

David W. Eisele, MD et al.,"Direct Hypoglossal Nerve Stimulation in Obstructive Sleep Apnea," Arch Otolaryngol Head Neck Surg., vol. 123, 1997, pp. 57–61.

David W. Eisele, MD et al. "The Effects of Selective Nerve Stimulationon on Upper Airway Airflow Mechanics,"Arch Otolaryngol Head Neck Surg., vol. 121, 1995, pp. 1361–1364.

David W. Fairbanks, MD et al., "Nuerostimulation for Obstructive Sleep Apnea: Investigations," ENT Journal, vol. 72, No. 1, 1993, pp. 52–57.

Iain C. Gleadhill et al., "Upper Airway Collapsibility in Snorers and in Patients with Obstructive Hypopnea and Apnea," Am Rev Respir. Dis., vol. 143, 1991, pp. 1300–1303.

George S. Goding, Jr., MD et al., "Relief of Upper Airway Obstruction with Hypoglossal Nerve Stimulation in the Canine," Laryngoscope, vol. 108, 1998, pp. 162–168.

Christian Guilleminault, MD et al., "The Effect of Electrical Stimulation on Obstructive Sleep Apnea Syndrome," Chest, vol. 107, 1995, pp. 67–73.

Joan C. Hendricks et al., "Upper Airway Dilating Muscle Hyperactivity During Non–Rapid Eye Movement Sleep in English Bulldogs," Am Rev Respir Dis, vol. 148, 1993, pp. 185–194.

Wataru Hida et al., "Hypoglossal Nerve Stimulation Affects the Pressure–Volume Behavior of the Upper Airway," American Journal of Respiratory and Critical Care Medicine,vol. 151, 1995, pp. 455–460.

Wataru Hida et al., "Submental Stimulation and Supraglottic Resistance During Mouth Breathing," Respiration Physiology, vol. 101, 1995, pp. 79–85.

B. Hillarp et al., "Videoradiography at Submental Electrical Stimulation During Apnea in Obstructive Sleep Apnea Syndrome," Acta Radiologica, vol. 32, 1991, pp. 256–259.

R.L. Horner et al., "Sites and Sizes of Fat Deposits Around the Pharynx in Obese Patients with Obstructive Sleep Apnoea and Weight Matched Controls," Eur Respir J., vol. 2, 1989, pp. 613–622.

Faiq G. Issa et al., "Genioglossus and Breathing Responses to Airway Occlusion: Effect of Sleep and Route of Occlusion," J. Appl. Physio., vol. 64 No. 2, 1988, pp. 543–549.

R. John Kimoff et al., "Mechanisms of Apnea Termination in Obstructive Sleep Apnea," American Journal of Respiratory and Critical Care Medicine, vol. 149, 1994, pp. 707–714.

Hiroshi Kiimura et al., "The Effect of Hypoxic Depression on Genioglossal Muscle Activity in Healthy Subjects and Obstructive Sleep Apnea Patients," American Sleep Disorders Association and Sleep Research Society, vol. 16, 1993, pp. S135–S136.

Erik van Lunteren, M.D. et al., "The Muscles of the Upper Airways," Clinics in Chest Medicine, vol. 7, No. 2, 1986, pp. 171–188.

William S. Mezzanotte et al., "Waking Genioglossal Electromyogram in Sleep Apnea Patients Versus Normal Controls (a Neuromuscular Compensatory Mechanism)," The Journal of Clinical Investigation, Inc., vol. 89, 1992, pp. 1571–1579.

Miki Hiroshi et al., "A New Treatment for Obstructive Sleep Apnea Syndrome by Electrical Stimulation of Submental Region," Tohoku J. Exp. Med., vol. 154 No. 1, 1988, pp. 91–92.

Miki Hiroshi et al., "Effects of Submental Electrical Stimulation During Sleep on Upper Airway Patency in Patients with Obstructive Sleep Apnea," Am Rev Respir Dis., vol. 140, 1989, 1285–1289.

D.L. Morrison et al., "Pharyngeal Narrowing and Closing Pressures in Patients with Obstructive Sleep Apnea," Am Rev Respir Dis., vol. 148, 1993, pp. 606–611.

H. Bishara et al., "Electrically–Activated Dilator Muscles Reduce Pharyngeal Resistance in Anaesthetized Dogs with Upper Airway Obstruction," Eur Respir J., vol. 8, 1995, pp. 1537–1542.

Odeh Majed et al., "Dependency of Upper Airway Patency on Head Position: The Effect of Muscle Contraction," Respiration Physiology, vol. 100, 1995, pp. 239–244.

A. Oliven et al., "Improved Upper Airway Patency Elicited by Electrical Stimulation of the Hypoglossus Nerves," Respiration, vol. 63, 1996, pp. 213–216.

Onal Urgun et al., "Periodic Breathing and the Pathogenesis of Occlusive Sleep Apneas," Am Rev Respir Dis., vol. 126, 1982, pp. 676–680.

Anthony T. Scardella et al., "Strength and Endurance Characteristics of the Normal Human Genioglossus," Am Rev Respir Dis., vol. 148, 1993, pp. 179–184.

R.P. Schnall, et al., "Dilatory Effects of Upper Airway Muscle Contraction Induced by Electrical Stimulation in Awake Humans," J. Appl. Physiol., vol. 78 No. 5, 1995, pp. 1950–1956.

Alan R. Schwartz et al., "Electrical Stimulation of the Lingual Musculature in Obstructive Sleep Apnea," J. Appl. Physiol, vol. 81 No. 2, 1996, pp. 643–652.

Alan R. Schwartz, M.D. "Hypoglossal Nerve Stimulation in Obstructive Sleep Apnea," APSS Post Graduate Course, May 30, 1995, pp. 1–9.

Richard S. Schwartz, DDS et al., "Effects of Electrical Stimulation to the Soft Palate on Snoring and Obstructive Sleep Apnea," Dec. 20, 1995, pp. 1–17.

Karen Eller Shelton et al., "Paryngeal Fat in Obstructive Sleep Apnea," Am Rev Respir Dis., vol. 148, 1993, pp. 462–466.

John W. Shepard, Jr. et al., "Localization of Upper Airway Collapse During Sleep in Patients with Obstructive Sleep Apnea," Am Rev Respir Dis., vol. 141, 1990, pp. 1350–1355.

Douglas J. Tangel et al., "Influence of Sleep on Tensor Palatini EMG and Upper Airway Resistance in Normal Men," J. Appl. Physiol., vol. 70 No. 6, 1991, pp. 2574–2581.

Zoltan Tomori et al., "Reflex Reversal of Apnoeic Episodes by Electrical Stimulation of Upper Airway in Cats," Respiration Physiology, vol. 102, 1995, pp. 175–185.

John R. Wheatley et al., "Influence of Sleep on Genioglossus Muscle Activation by Negative Pressure in Normal Men," Am Rev Respir Dis., vol. 148, 1993, 597–605.

John R. Wheatley et al., "The Influence of Sleep on Pharyngeal Reflexes," American Sleep Disorders Association and Sleep Research Society, vol. 16, 1993, pp. S87–S89.

Laurel Wiegand et al., "Collapsibility of the Human Upper Airway During Normal Sleep," J. Appl. Physiol., vol. 66 No. 4, 1989, pp. 1800–1808.

* cited by examiner

INTRAORAL ELECTROMUSCULAR STIMULATING DEVICE AND METHOD

CROSS-REFERENCE TO RELATED APPLICATIONS

This is a Continuation of U.S. patent appln. Ser. No. 09/436,857 filed Nov. 9, 1999, now U.S. Pat. No. 6,212,435 issued Apr. 4, 2001, which claims priority under 35 U.S.C. §119(e) from provisional U.S. patent appln Ser. No. 60/108,408 filed Nov. 13, 1998.

BACKGROUND OF THE INVENTION

1. Field of the Invention

The present invention pertains to a device and method for providing non-invasive intraoral electromuscular stimulation to a patient to treat a breathing disorder, such as obstructive sleep apnea, and, in particular, to a device and method wherein electromuscular stimulation is provided to the patient at a time prior to the onset of inspiration and continues through a major portion of the inspiratory phase and is applied at a level sufficient to induce muscle contraction without pain and/or is provided bilaterally at sublingual locations posterior to the frenulum in an anterior-to-posterior and/or posterior-to-anterior direction.

2. Description of the Related Art

Obstructive sleep apnea (OSA) is a medical condition in which the upper airway is repeatedly occluded during sleep despite continued respiratory effort. Those afflicted with OSA experience sleep fragmentation and complete or nearly complete cessation of ventilation intermittently during sleep with potentially severe degrees of oxyhemoglobin desaturation. An OSA sufferer typically experiences many apnea and/or hyponea events throughout the night. During an apnea event, the resulting hypoxia typically progresses until arousal occurs, which reestablishes airway patency.

Symptoms of OSA include snoring, choking and/or gasping during sleep, fragmented sleep, daytime sleepiness, fatigue and poor concentration. Airway obstruction can lead to a reduction in tidal volume, oxygen desaturation and progressive increases in respiratory rate. The long-term effects of OSA may be translated clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during wakefulness, as well as during sleep, and continuous reduced arterial oxygen tension. Hypersomnolent sleep apnea patients may be at risk for excessive mortality from these factors as well as by an elevated risk for accidents while driving and/or operating potentially dangerous equipment.

Studies of the mechanism of collapse of the airway suggest that during some stages of sleep, there is a general relaxation of the muscles that stabilize the upper airway segment. This general relaxation of the muscles is believed to be a factor contributing to OSA. More specifically, it is generally understood that the patency of the airway depends on the activity of the pharyngeal dilator muscles. Common sites of obstruction are behind the tongue and at the level of the soft palate. In a normal state, the muscles of the tongue, the genioglossus, hyoglossus, styloglossus, palatoglossus and the superior, inferior, transverse and vertical linguals, act to protrude or retract the tongue. Posterior fibers of the genioglossus draw the base of the tongue forward and anteriorly. One or more of these muscles normally contract reflexively during inspiration. However, it is generally understood that OSA suffers experience a reduction of lingual muscle activity during sleep as compared to nonapneics, thereby causing a reduction in airway patency.

Several therapeutic remedies exist for treating OSA. The most invasive, yet most likely to be successful, is a tracheotomy, which creates an airway bypass around the site of obstruction. Other surgical remedies include removal of deformed, loose or swollen structures or tissues in the upper airway. It is also known to apply positive air pressure at the mouth and/or nose of the patient to "splint" the airway, thereby maintaining an open passage to the lungs. In addition, pharmacological solutions have also been pursued.

None of these therapies is successful in all cases. Surgical relief is invasive, introduces a potential for surgical complications and is appropriate in only a small percentage of cases. On the other hand, the nasal or nasal/oral mask needed to apply a positive air pressure is not tolerated by some OSA patients. Pharmacological therapies have been, in general, less than satisfactory, and side effects are frequent.

It is also been proposed to treat OSA by electrically stimulating the musculature of the upper airway to prevent its relaxation and/or induce contraction, thereby preventing or minimizing subsequent blockage of the airway. There are two methods in which electromuscular stimulation can be applied to a patient; invasively or non-invasively. Invasive electrical stimulation of a muscle involves implanting one or more electrodes, either permanently or temporarily within the patient. These subcutaneous electrodes are typically located on or near the nerves that control the muscle to be stimulated. In some applications, the electrodes are placed in direct contact with the target muscle. Subcutaneous electrodes positioned adjacent the muscle or on or near the nerve controlling the muscle to be stimulated have the benefit of focusing the electrical energy on the muscle/nerve to be stimulated.

However, electrical muscle stimulation utilizing implanted electrodes requires surgical intervention, the permanent presence of foreign materials within the patient's tissue, and, in some applications, at least one electrical connection protruding from the patient. Consequently, there is a potential for infection or irritation at the surgical site and at the site where the electrode or electrical connection protrudes through the surface of the patient. In addition, it is reasonable to expect that some patients may be apprehensive about having a foreign object surgically placed within their body.

Non-invasive electrical stimulation of the muscles in the upper airway involves placing an electrode in direct contact with a surface of the patient and passing a current through the surface tissues adjacent the electrode. For example, U.S. Pat. No. 5,123,425 to Shannon et al. teaches applying an electrical stimulation to the exterior surface of the patient's neck below the chin to induce contraction of the upper airway muscles. In addition, U.S. Pat. No. 5,792,067 to Karell teaches an intraoral device that applies electrical stimulation to the hard palate, soft palate or pharyngeal area to induce contraction of the upper airway muscles. U.S. Pat. No. 5,190,053 to Meer teaches an intraoral device that applies electrical stimulation to the genioglossus muscle via electrodes located on the mucosa on the floor of the mouth on either side of the frenulum, which is the connecting membrane under the tongue that attaches the anterior portion of the tongue to the floor of the mouth.

While each of these non-invasive stimulation techniques claim to achieve some degree of success in opening the airway, it not clear that they are successful in a sufficient number of patients to render any one of these techniques a viable replacement to the other conventional treatments discussed above.

In addition to using either invasive or non-invasive stimulation on a patient, conventional electromuscular stimulation treatments typically initiate stimulation in one of two alternative timing methods. In a first timing method, stimulation is applied only when needed to counteract a detected breathing disorder, for example, at the onset of an apnea or when snoring is detected. This technique has the advantages of, for example, conserving energy and minimizing muscle fatigue. However, it is not clear that this stimulation timing method is sufficiently successful in breaking an apnea or stopping snoring in a significant number of OSA sufferers to be suitable for widescale and/or practical use.

According to a second timing method, stimulation is provided independent of the occurrence of a breathing disorder, such as an apnea, snore or other symptoms of respiratory distress. In this second method, stimulation is typically provided during each inhalation phase of a patient's breathing cycle and typically is initiated at the onset of inspiration. For example, U.S. Pat. Nos. 5,540,732 and 5,522,862 both to Testerman teach an invasive electrical stimulation system in which stimulation is applied to the patient in response to sensed inspiration. In an alternative method, such as that taught by U.S. Pat. No. 5,158,080 to Kallok, stimulation is provided at all times during the patient's breathing cycle, i.e., during the entire inspiratory phase and the entire expiratory phase. Although some success has been claimed when stimulation is provided independent of the occurrence of a breathing disorder, it not clear that the degree of success of either technique is sufficient to warrant the use such a timing technique on a widescale basis.

Other investigators, such as R. P. Schnall et al., as indicated, for example, in an article entitled "Dilatory Effects of Upper Airway Muscle Contraction Induced by Electrical Stimulation in Awake Humans," published in Volume 75 of the Journal of Applied Physiology in 1995, pages 1950–65, have experimented with various stimulation techniques, including the timing at which stimulation is initiated and the corresponding placement of the electrodes within the patient. However, as concluded in this article, the stimulation techniques attempted by Mr. Schnall et al. were unsuccessful in decreasing the number of breathing disorder events occurring in the test patients.

SUMMARY OF THE INVENTION

Accordingly, it is an object of the present invention to provide an intraoral electromuscular stimulation device for treating a breathing disorder, such as OSA, that overcomes the shortcomings of conventional muscle stimulating devices. This object is achieved according to one embodiment of the present invention by providing an intraoral electromuscular stimulation device that delivers intraoral electrical stimulation to a patient to reduce or minimize airway closure. In one embodiment of the present invention, the electromuscular stimulation device includes a first electrode and a first support member that sublingually supports the first electrode in a position posterior to the frenulum and generally proximate to a first, second or third molar of the patient. The stimulation device also includes a second electrode and a second support member that sublingually supports the second electrode in a position posterior relative to the first electrode.

It is another object of the present invention to provide an electromuscular stimulating system for treating a breathing disorder that does not suffer from the disadvantages of conventional systems. This object is achieved by providing an electromuscular stimulating system that includes an intraoral electrode dental appliance and a stimulation unit associated therewith. The dental applicant includes a first electrode and a first support member that supports the first electrode in a sublingual position posterior to the frenulum and generally proximate to the first, second or third molar of a patient. The dental appliance also includes a second electrode and a second support member that supports the second electrode in a sublingual position posterior relative to the first electrode. The stimulation unit provides stimulating energy to a portion of the patient in an anterior-to-posterior or posterior-to-anterior direction via the first and second electrodes.

It is yet another embodiment of the present invention to provide a method of providing intraoral electromuscular simulation to the patient that overcomes the shortcomings of conventional electrical stimulation methods. This objects is achieved, according to one embodiment of the present invention, by providing a method that includes the steps of: (1) positioning a first electrode in a patient's mouth such that the first electrode is sublingually supported in a position posterior to the frenulum and generally proximate to one of a first, second or third molar, (2) positioning a second electrode in the patient's mouth such that the second electrode is sublingually supported in a position posterior relative to the first electrode, and (3) applying an electrical stimulation to a portion of the patient via the first electrode and the second electrode so that the stimulating current travels in either an anterior-to-posterior or a posterior-to-anterior direction in the patient.

It is a still further object of the present invention to provide an intraoral electromuscular stimulation device employing a stimulation technique that applies stimulation to the patient at an appropriate time, duration, location and energy level so as to achieve results that are an improvement over conventional methods. This object is achieved by providing an intraoral electromuscular stimulation device that includes a first electrode, a second electrode, a first support member that sublingually supports the first electrode on a first side of the patient's mouth relative to his or her midline, a second support member that sublingually supports the second electrode in a posterior position relative to the first electrode on the same side of the patient's mouth, a sensor that detects a respiratory parameter of the patient and outputs a signal indicative thereof, and a control unit operatively coupled to the sensor, first electrode and second electrode. The control unit receives the signal from the sensor, distinguishes between inspiration and expiration of a patient based thereon, and initiates an electrical stimulation of the patient in an anterior-to-posterior or posterior-to-anterior direction via the first and the second electrodes at a start time prior to the onset of inspiration. The control unit also continues the stimulation through a portion of the inspiratory phase and provides the stimulation at a level that is sufficient to induce muscle contraction but is not sufficient to cause the patient pain.

It is still another embodiment of the present invention to provide a method of providing intraoral electromuscular simulation that applies stimulation to the patient at an appropriate time, duration and energy level so as to achieve results that are an improvement over conventional methods. This object is achieved, according to one embodiment of the present invention, by providing a method that includes the steps of: (1) positioning a first electrode and a second electrode in sublingual positions within a patient's oral cavity on the same side of the patient's mouth relative to the midline, with the second electrode being positioned posterior relative to the first electrode, (2) detecting a respiratory parameter of a patient and providing a signal indicative thereof, wherein the respiratory parameter is any monitorable physiological condition that can be used to differentiate between inspiration and expiration of the patient, and (3) applying an electrical stimulation to a portion of the patient between the first and second electrodes in a posterior-to-anterior direction or an anterior-to-posterior direction. In this embodiment of the present invention, initiating application of electrical stimulation occurs at a stimulation time prior to onset of inspiration, continues through a portion of the inspiratory phase and is provided at a level that is sufficient to induce muscle contraction but not cause the patient pain.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
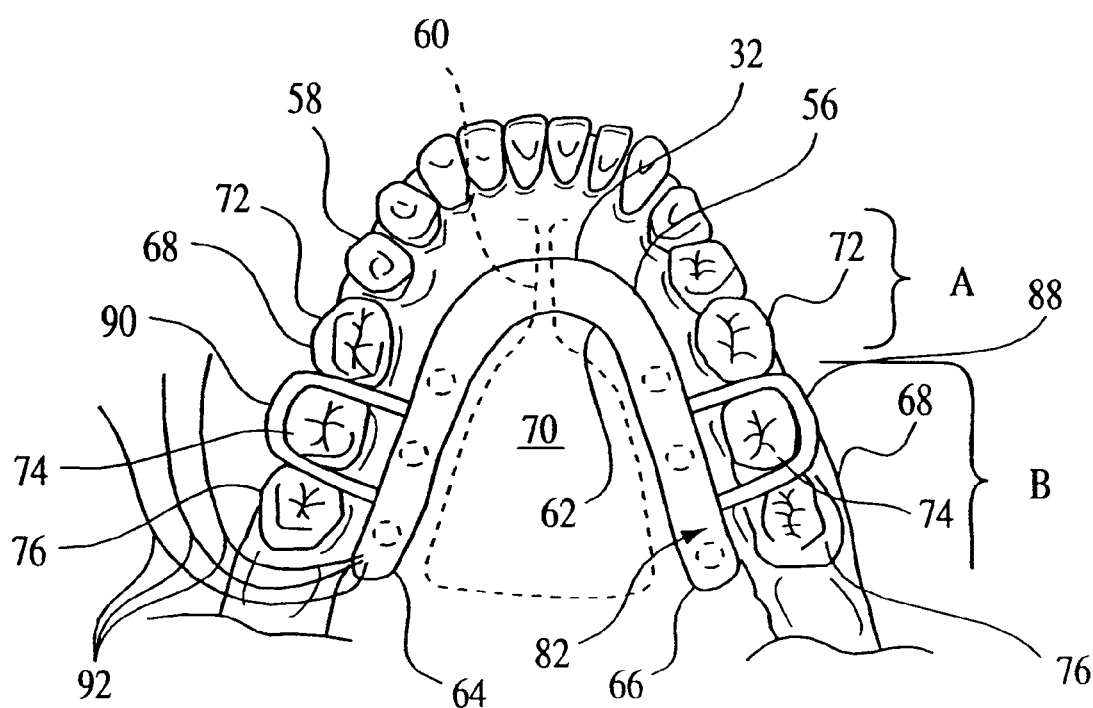
FIG. 1 is a plan view of an exemplary embodiment of a dental appliance used with a first embodiment of the electromuscular stimulating system of the present invention shown positioned relative to a patient's lower teeth.
Figure 2:
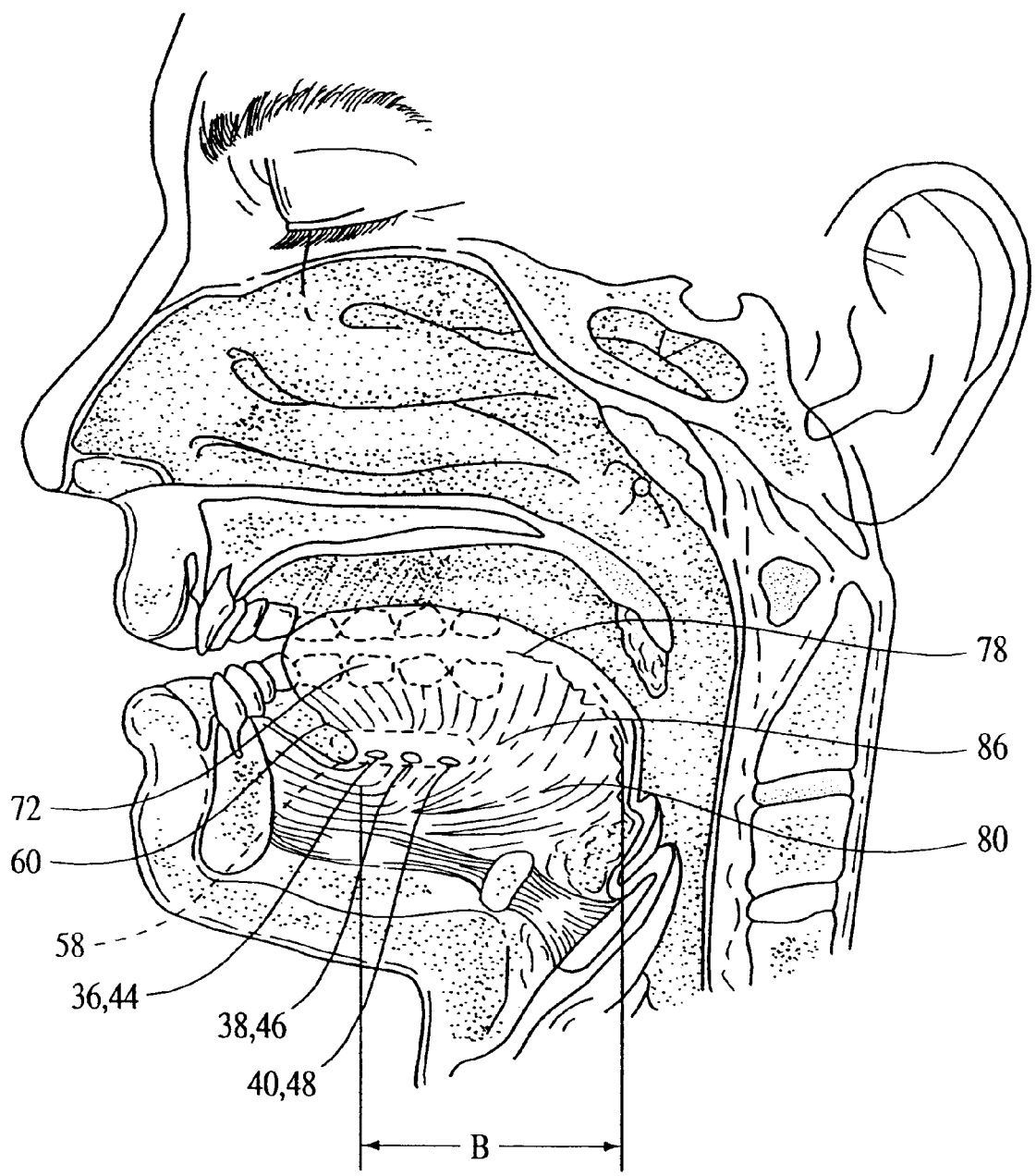
FIG. 2 is a side sectional view of a patient illustrating the sites of stimulation for the device illustrated in FIG. 1.
Figure 3:
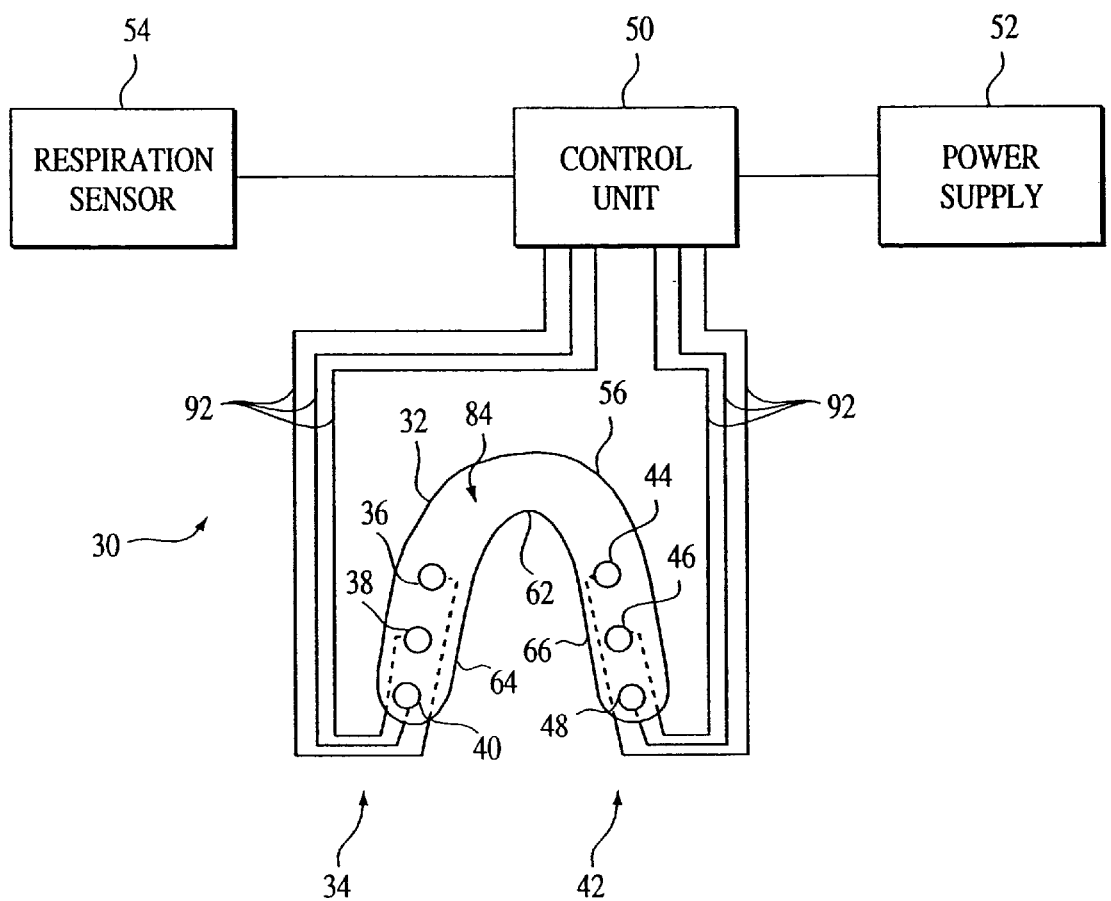
FIG. 3 is a schematic diagram of an electromuscular stimulating system according to a first embodiment of the present invention.

Referring now to FIGS. 1–3 there is shown therein a first embodiment of an electromuscular stimulating system 30 of the present invention for providing sublingual electromuscular stimulation to a patient to reduce or minimize the occurrence of a breathing disorder, such as OSA. As best illustrated schematically in FIG. 3, electromuscular stimulating system 30 includes a dental appliance 32 on which are provided a first group 34 of electrodes 36, 38 and 40 and a second group 42 of electrodes 44, 46 and 48. During normal use, dental appliance 32 is located under the patient's tongue so that the electrodes are in contact with the patient at sublingual locations generally proximate to the sublingual musculature to provide electrical stimulation to the muscles of the upper airway responsible for maintaining the patency of the airway. Electromuscular stimulating system 30 includes a control unit 50 that controls the application of stimulation pulses to the electrodes, a power supply 52 for running the system and for supplying the stimulation energy, and a respiration sensor 54 for detecting a physiological characteristic of the patient indicative to the patient's breathing. The details of each component and its function in electromuscular stimulating system 30 are discussed in greater detail below.

In the illustrated embodiment, first and second groups of electrodes 34 and 42 are located on a common, unitary support member 56. It is to be understood, however, that the present invention contemplates providing each group of electrodes, pairs of electrodes, and/or individual electrodes on a separate support member. In addition, although first and second groups of electrodes 34 and 42 are illustrated as each having three individual electrodes, it is to be understood that as few as two electrodes can be provided in each group so long as at least one pair of (two) electrodes are sublingually located on each side of the patient's oral cavity, i.e., located on each side of the patient's midline within the oral cavity. Conversely, first and second groups of electrodes 34 and 42 can each include more than the three electrodes shown in the figures, depending on the stimulation pattern to be achieved.

Support member 56 is sized so as to fit under the patient's tongue proximate to the mandibular, i.e., lower, teeth 58, as generally shown in FIG. 1. Once properly positioned, the patient's frenulum 60 is located adjacent curve 62 in support member 56. In addition, each lateral arm 64 and 66 of support member 56 extends posteriorly into the patient's oral cavity sublingually with teeth/gum tissues 68 being located on one side of the support member and the tongue/genioglossus muscle tissue 70, the outline of which is illustrated by the dashed line in FIG. 1, being located on the other. Support member 56 is sized and configured and the electrodes disposed thereon are arranged and configured such that, once properly positioned, all of the electrodes are sublingually located within the patient in a position posterior to the frenulum 60 during normal use.

As mentioned briefly above, the frenulum is a thin membrane generally located along the centerline of the mouth that connects the underside of the tongue to the floor of the mouth. In a normal human, the frenulum is on the order of a few fibers thick and rapidly thickens in an anterior-to-posterior direction along the centerline of the mouth. The tissue commonly referred to as the frenulum ceases in an anterior-to-posterior direction at an undefined point where there is no longer a thin membrane in the lateral direction, i.e., a direction perpendicular to the centerline, of the mouth. The transition from the region below the tongue corresponding to the patient's frenulum, which is identified as region A in FIG. 1, to the area of the mouth below the tongue where there is no longer a thin membrane in the lateral direction and, hence, no frenulum, which is identified as region B, generally occurs at a first molar 72.

The present inventors discovered that optimal results from electromuscular stimulation are achieved when the stimulating electrodes are sublingually located in a generally posterior position within the oral cavity. Thus, the present invention contemplates locating the stimulating electrodes in region B, which is posterior to region A corresponding to frenulum 60, so that all of the electrodes are posterior to frenulum 60. The present inventors postulate that non-invasive, sublingual stimulation of the patient in a generally posterior location in the patient's mouth induces contraction or prevents relaxation of a posterior portion of the genioglossus, which is believed to be a portion of the genioglossus muscle that significantly affects the degree of opening of the airway.

FIGS. 1 and 2 illustrate an example of the location of electrodes 36–40 and 44–48 relative to the anatomical features of the patient according to a presently preferred embodiment of the present invention. As shown, the most anterior electrodes 36 and 44 are generally proximate to first molar 72, middle electrodes 38 and 46 are generally proximate to a second molar 74, and the most posterior electrodes 40 and 48 are generally proximate to the third molar (wisdom tooth) 76, if present in the patient. In addition, electrodes 36–40 and 44–48 are located under tongue 78 in a position generally overlying the middle or posterior portion of genioglossus muscle 80. Although FIGS. 1 and 2 illustrate electrodes 36–40 and 44–48 as being generally aligned with a tooth in the patient's mouth, it is to be understood, however, that aligning the electrodes with the teeth is not necessary. Furthermore, the dental appliance and associated electrodes can have a variety of configurations so long as all of the electrodes are sublingually located within the patient within region B, which is the region posterior to the frenulum 60 and that continues in a posterior direction until it is no longer possible for an electrode located therein to stimulate the genioglossus muscle. That is, region B encompasses the area under the tongue that begins at the termination point of the frenulum and extends in a posterior direction to the esophagus. See FIG. 2.

The present invention contemplates that the electrodes in each group of electrodes, i.e., the electrodes located on the same side of the patient's mouth or on the same lateral arm, are arranged so that at least one electrode is posterior to another electrode. For example, in FIG. 3, electrode 38 is posterior to electrode 36 and electrode 40 is posterior to electrodes 36 and 38 during normal use. Locating the electrodes in each group within the patient in these positions relative to one another is done because the present inventors also discovered that optimum stimulation results are achieved if the stimulation current flow through the patient is in a generally anterior-to-posterior or posterior-to-anterior direction. The present inventors postulate that these directions for current flow optimize contraction because the direction of current flow through the relevant portions of the genioglossus coincides with the direction of the muscle tissue and/or nerve directions at that location.

In the embodiment illustrated in FIG. 1, electrodes 36–40 and 44–48 are imbedded in the support member 56 on a common surface 84 so that once support member 56 is inserted under the tongue, electrodes 34–38 and 42–46 are in contact with the patient's tissue at the lower portion of the oral cavity proximate to the sublingual musculature. In the illustrated embodiment, for example, surface 84, on which electrodes 36–40 and 44–48 are located, corresponds to the inferior surface of support member 56 and is opposite superior surface 82. In this embodiment, inferior surface 84 generally faces the patient's jaw and superior surface 82 generally faces the patient's hard palate when the dental appliance is properly positioned within the patient.

It is to be understood, however, that the present invention contemplates locating the electrodes at other locations within the mouth or at other locations on the support member so long as the electrodes are located sublingually posterior to the frenulum. For example, the electrodes can be located on a side surface, rather than a top or bottom surface, of support member 56, so that the electrodes face a base area 86 of the tongue, which is the area where the genioglossus transitions into the tongue tissue. Also, the surfaces on which the electrodes are disposed need not be planar. For example, the portions of the surface on which the electrodes are disposed can be raised to facilitate contact of the electrodes with the patient. Furthermore, the electrodes themselves need not be planar, but may be a raise mound of conductive material, for example. The present invention contemplates providing the electrodes at locations on the support member and/or having shapes other than that shown in the figures so long as the goals of the present invention as discussed herein are achieved.

Electrodes 36–40 and 44–48 can be made from a variety of conductive materials. More specifically, the electrodes can be made from any electroconductive material suitable for use in the intraoral environment, and, preferably, from a material suitable for long term use in such an environment. Each electrode can be made from the same or different materials. Examples, of suitable materials include, but are not limited to, metal, carbon-impregnated metal or plastic, and electroconductive rubber or gels.

Electrodes 36–40 and 44–48 can have a variety of configurations depending on the desired stimulation pattern so long as they are capable of exchanging electric current with the tissue contacting the electrode. For example, the electrodes can be strip electrodes having one of a variety of patterns, rather than the spot electrodes shown in the figures. The shapes of the electrodes in each group can be the same or can differ from one electrode to the next, and the electrodes in one group need not have the same configuration as the electrodes in another group. The electrodes disposed on support member 56 are illustrated by dashed lines in FIG. 1 because they are located on the underside of support member 56 when viewed from the top as shown in FIG. 1.

Support member 56 includes a mechanism for attaching the support member to the patient. In the illustrated embodiment, a pair of attaching members 88 and 90 are disposed on either side of the support member. The present invention contemplates that attaching members 88 and 90 are any structure capable of being secured to the patient's lower teeth or other jaw structure to maintain the electrodes in a substantially fixed position relative to the lower teeth. In a preferred embodiment of the present invention, however, the electrodes are moveable in a generally an up and down direction within the patient so that the electrodes are maintained in contact with the floor of the mouth posterior to the frenulum. It is further preferable that there be minimal movement of the electrodes in the anterior-posterior or posterior-anterior direction and in the medial-lateral or lateral-medial direction so long as the electrodes are maintained in contact with the patient's tissues. Any configuration for the support members that provides these functions are contemplated within the scope of the present invention.

In the embodiment illustrated in FIG. 1, attaching members 88 and 90 are wire-like bands that are generally wrapped around at least a portion of single tooth. It is to be understood, however, that the size of each attaching member can be made larger to attach to more than one tooth. Attaching members 88 and 90 are made from any suitable biocompatible material having sufficient strength to attach support member to the patient yet moldable to permit a common (non deformed) configuration of the attaching members to be formed to fit a wide variety of patients having a variety of different dental configurations. It should be noted that if more than one support member is provided, each support member should include a mechanism for attaching that support member to the patient.

It is to be further understood, that the support members need not be rigidly attached to the teeth. On the contrary, other embodiments of the present invention contemplate that the attaching mechanism be flexible enough to permit slight movement of the support member or support members. Making the attachment of the support member to the teeth somewhat flexible is believed to increase patient comfort. In addition, the present invention contemplates providing a biasing mechanism so that the support member and/or electrodes are urged into contact with the patient's tissue. An example of a suitable biasing mechanism is to make the arms of attaching members 88 and 90 spring-like so that the attached support members are urged into contact with the patient.

While the attaching members are illustrated in FIG. 1 as being a wire or wire-like configuration, it is to be understood that the present invention is not limited to such a structure. On the contrary, the present invention contemplates that any mechanism for attaching the electrodes to the patient can be used for the attaching member. For example, a molded member, rather than a metal or metal-like strip can be used to secure the support member within the patient. The moldable member can be a premolded appliance that generally matches the patient's teeth or a customizable mold that can be configured to match the tooth pattern of a specific patient. The present invention also contemplates that the attaching member can be secured to the upper teeth so long as additional support members are provided for sublingually locating the electrodes at the positions discussed above. The present invention further contemplates using a biocompatible adhesive to secure the electrodes at the appropriate location within the patient, without any attachment to the teeth.

In yet another variation, more permanent devices can be used for securing the support member within the oral cavity. For example, a patient may be provided with a support stem that is permanently fixed to the jaw bone or to a nearby existing tooth or tooth root. In this embodiment, the support member for the electrodes should be provided with a coupling member suitable for attaching to the stem so that the support member can be selectively attached to the relatively permanent mount within the patient's mouth.

According to one embodiment of the present invention, electrical stimulation is provided to the patient during selected portions of the patient's breathing cycle independent of the occurrence of a breathing disorder, such as an apnea, snore or other symptoms of respiratory distress. This technique requires sensing the patient's breathing and distinguishing between the inspiratory phase and the expiratory phase of the breathing cycle so that electrical stimulation can be applied during the desired portion or portions of the breathing cycle. Sensing the patient's breathing is accomplished by respiration sensor 54. See FIG. 1. Respiration sensor 54 is any device suitable to detect the respiration, i.e., breathing, of the patient. For example, respiration sensor 54 can be a thermister or thermocouple device that detects temperature changes associated with the exchange of gas with the patient, a plesmography or inductance belt that detects the respiratory efforts of the patient, or a flow sensor in communication with the patient's airway that monitors the flow of gas to and/or from the patient. It is to be understood that this list of exemplary sensing device is not comprehensive or exclusive. On the contrary, the present invention contemplates using as sensor 54 any sensor device that detects a physiological condition of the patient suitable for differentiating between the inspiratory and the expiratory phases of the breathing cycle and that can output signals indicative thereof. Other suitable sensing devices may measure, for example, the patient's EMG activity or may be acoustically based, to provide an indication of the patient's respiratory state.

Power supply 52 is any power source suitable to provide power to control unit 50, respiration sensor 54 (if necessary) and the electrodes in dental appliance 32. Examples, of suitable power supplies are conventional AC power and batteries. Preferably, power supply 52 or control unit 50 includes safety features, such as a fuse, surge protector, circuit breaker or optical isolation to prevent fluctuations in the power supply from adversely affecting the electromuscular stimulation system.

Control unit 50 is any suitable processor that can receive an input, such as the input from respiration sensor 54, and based thereon, cause an electrical stimulation energy to be provided to the patient via the electrodes. Furthermore, control unit 50 and/or power supply 52 collectively contain the necessary components for providing electrical stimulation energy to the patient. For example, one embodiment of the present invention contemplates that control unit 50 includes a pulse generator that provides a series of pulses to the electrodes to stimulate the patient, with the pulse generator being powered via power supply 52. It is to be understood, however, that power supply 52 can include all of the necessary components for generating and shaping the pulse waveform, with the control unit providing the necessary components for gating the flow of the pulses from the power supply. In addition, control unit 50 includes circuitry or components for selecting which electrodes are to receive the stimulation energy from the power supply. In FIG. 3, the electrodes are connected to the control unit via hardwires 92. The control unit selects which conductors in hardwires 92 are to be provided with stimulation energy. For example, one may desire to stimulate across electrodes 36–38 and thereafter across electrodes 36–40. The control unit can be programmed to provide such a stimulation pattern by selecting the appropriate conductors to which to provide the electrical energy and the appropriate timing pattern.

According to one embodiment of the present invention, control unit 50 includes manually operable actuating mechanisms, such as buttons, dials, knobs or switches, for performing functions such as activating and deactivating the unit, setting the ranges for the output energy strength and/or duration, setting threshold values, setting operating modes, setting pulse frequency and/or duty cycle and conducting diagnostic routines on the electromuscular stimulating system. The present invention also contemplates that a common control unit can be used in conjunction with a plurality of sensors 54, a plurality of dental appliances 32, and/or a plurality of sensor-dental appliance combinations. If one control unit is being used in conjunction with a plurality of sensors, a plurality of dental appliances, and/or a plurality of sensor-dental appliance combinations, that control unit would include a plurality of additional input/output interfaces for connecting the additional sensors, dental appliances, and/or sensor-dental appliance combinations thereto.

The control unit can also be configured with any appropriate input/output interface for exchanging data between the control unit and an external source. For example, one or more interfaces can be provided for accessing, modifying, or downloading data stored in the control unit. Such data exchange interfaces can include, but are not limited to, an RS-232 port, modem, coaxial, optical fiber, rf, infrared, ultrasonic, or other interfaces that permit data exchange between the control unit and the external device. For example, data can be provided to the control unit using manual input devices, such as knobs, switches, buttons, and/or keypads coupled to or integral with the control unit. Data can also be provided to, modified or extracted from the control unit using an external computer that communicates with the control unit using an appropriate interface.

Control unit 50 and/or dental appliance 32 can further include warning devices, such as an audio indicator and/or a visual indicator, that inform the user, or a person monitoring the user, of the condition of the patient and/or electromuscular stimulating system 30. For example, an audio or visual warning can be generated if the patient has stopped breathing for a predetermined period of time, has begun or has stopped snoring, and/or has removed or inserted the dental appliance. Of course, an appropriate sensor or plurality of sensors for sensing such conditions must be provided. For example, a galvanic sensor can be provided on the dental appliance to detect when it is in contact with the patent.

As noted above, the present invention also contemplates providing warning signals indicative of the status of the electromuscular stimulating system. For example, an audio or visual warning signal can be generated if the dental appliance exceeds a predetermined temperature, if the power provided to the control unit, the sensors, or the dental appliance has been shut off, falls below a predetermined level or exceeds a predetermined level, if the sensors or the electrodes are not working, have become disconnected or fail to communicate with the control unit, and/or if there is a short in the system.

In addition to or in place of the relatively simple audio/visual warning indicators, other warning devices can be provided. For example, control unit 50 can include circuitry for notifying a remotely located third party of the existence of the condition causing the warning, using, for example, signals communicated via telephone lines. Furthermore, the warning signals, as well as other signals indicative of the condition of the patient and/or the electromuscular stimulating system that do not constitute a warning, can be provided to a display device, such as a monitor or LED. Such a display system may be particularly beneficial in a sleep lab setting where a single control unit is being used to monitor and stimulate a plurality of patients under the supervision of a sleep lab technician.

Figure 4A:
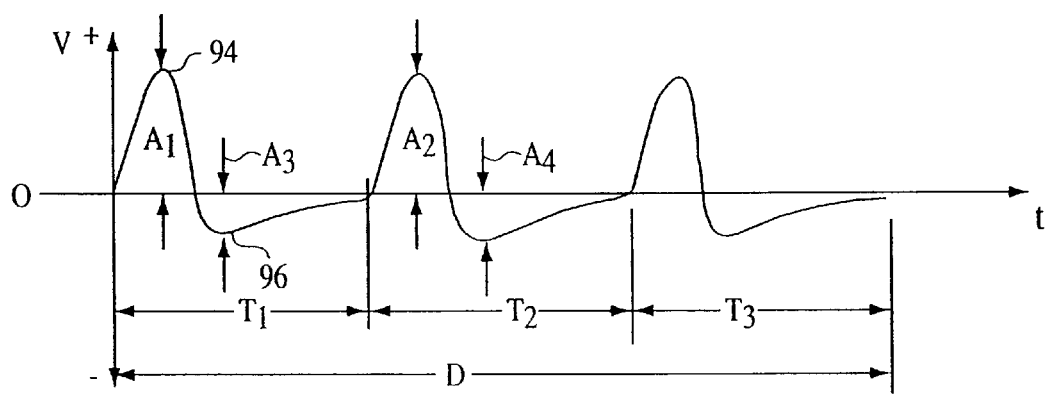
FIG. 4A is a waveform illustrating an exemplary train of stimulation pulses provided to the patient by the electromuscular stimulating system of the present invention and FIG. 4B is an presently preferred embodiment for the stimulating pulse.

An example of the stimulation pulses provided to the patient via electromuscular stimulating system 30 are shown in FIG. 4A. In the illustrated embodiment, the simulation pulses are a series of bipolar pulses, each pulse having a positive peak 94 and a negative peak 96. The series of bipolar pulses are in the form of a pulse train having a period D and are provided across any two electrodes in the same group of electrodes as a differential signal, so that a stimulating current passes through the patient in an anterior-to-posterior or posterior-to-anterior direction. For example, if the stimulation pulse is provided across electrodes 36 and 38 in electrode group 34, the stimulating current passes through the patient between these two electrodes. Because of the positioning of the electrodes within the oral cavity as discussed above, these electrodes are in an anterior-to-posterior relation so that the stimulating current flow through the patient is in an anterior-to-posterior or posterior-to-anterior direction. It should be understood that the present invention contemplates providing the stimulating pulse across any two electrodes in the same electrode group, i.e., on the same side of the patient's oral cavity, such as between electrodes 36–38, 38–40 and 36–40, so long as the direction of stimulation is in an anterior-to-posterior or posterior-to-anterior direction.

The present invention contemplates providing a pulse train that includes one or more stimulating pulses. The details of an exemplary embodiment of a pulse train are discussed below with reference to FIGS. 4A and 4B and the details of the stimulation technique according to one embodiment of the present invention are discussed below with reference to FIGS. 5A–5D. It is to be understood that the waveforms shown in these figures are not to scale. The characteristics of the stimulating pulses in the pulse train and the number of such pulses providing during a stimulation interval D, which is the time period during which muscle stimulation is to be achieved and corresponds to the duration of the pulse train, can vary depending on the amount of stimulating energy to be provided to the patient. For example, the present invention contemplates providing a train of stimulating pulses, wherein each pulse in the pulse train has the same general shape, as shown, for example, in FIG. 4B. It is further preferable that the stimulation energy be provided to the patient using a current controlled stimulation device, as opposed to a voltage controller, because it has been discerned by the present inventors that the voltage of the pulse applied to the patient tends to float or vary with the tissue characteristics, and, in particular, tissue resistivity, of the patient.

Figure 4B:
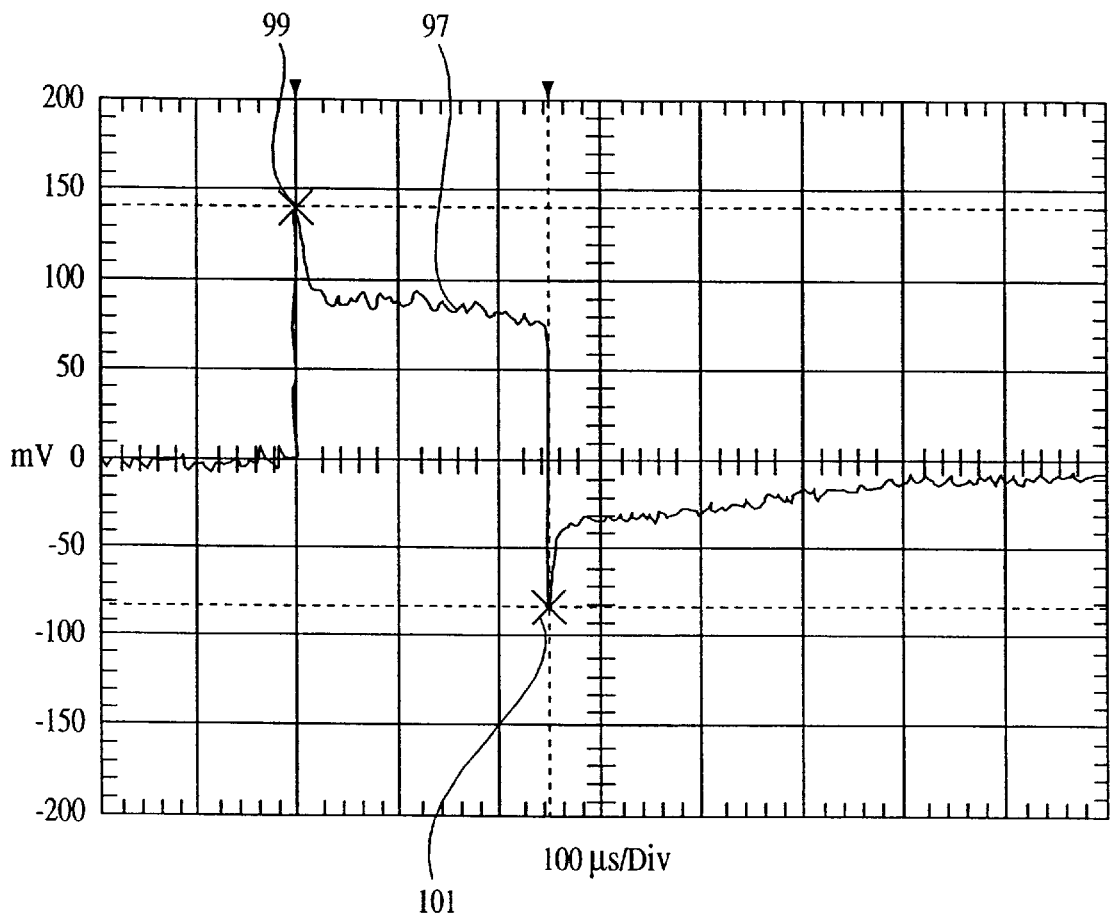

The present invention further contemplates that the features of the pulse train and/or the pulses in the pulse train, such as the amplitudes (positive and/or negative) $A_1, A_2, A_3, A_4, \ldots, A_n$ and durations $T_1, T_2, T_3, \ldots, T_n$ of the individual pulses in the pulse train, the duty ratio of the stimulating pulses in the pulse train, as well as duration D of the pulse train, can be varied to control the stimulation energy provided to the patient. These variables can be set by the control unit using any suitable interface and commonly vary from patient to patient. A presently preferred embodiment of a single stimulation pulse is illustrated in FIG. 4B. In this embodiment, the stimulation frequency is preferably in the range of 50–90 Hz.

It should be further noted that the shape of the pulses in the same pulse train need not be the same. On the contrary, the present invention contemplates providing a train of pulses (or a train having a single pulse) wherein the pulses in the pulse train have different or unique maximum peaks, minimum peaks, durations, shapes, frequencies so long as the function of adequately stimulating the patient to eliminate or reduce the breathing disorder without jeopardizing the health and safety of the patient are achieved. Of course, pulse shapes other than those illustrated in FIG. 4A, such as a square, sine, or triangle wave, can be used so long as this purpose is achieved.

For example, FIG. 4B illustrates a presently preferred embodiment of a pulse 97 for use with the electromuscular stimulation system of the present invention. Pulse 97 in FIG. 4B has a positive peak value 99 of approximately 140 mV and a negative peak value 101 of approximately −82 mV. It is to be understood, that these values can vary depending on the stimulation energy to applied to the patient so long as the energy level is sufficient to induce muscle contraction without causing pain.

By modifying the pulse shape, frequency and/or amplitude, the stimulation energy provided to the patient can be controlled. For example, it may be desirable, at least in some patients, to ramp the stimulation energy to its operating level over period D to minimize the potential for patient arousal that may result from the sudden onset of muscle contraction.

Figure 5A:
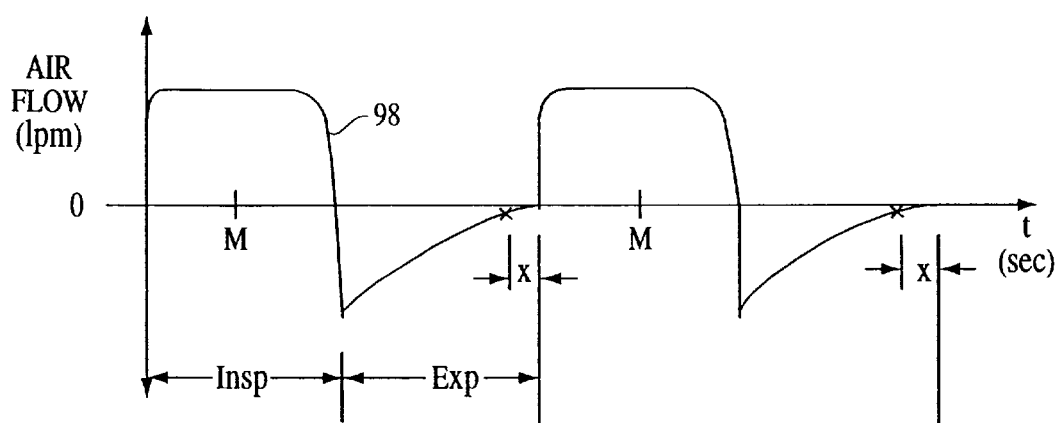
FIGS. 5A and 5B are waveforms of an airflow signal and a respiratory effort signal, respectively, illustrating the points for the onset of electrical stimulation according to the principles of the present invention.
Figure 5B:
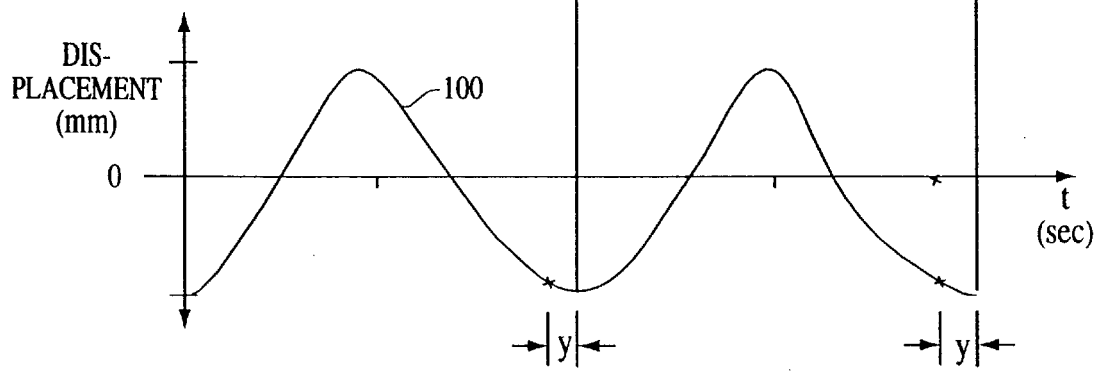
Figure 5C:
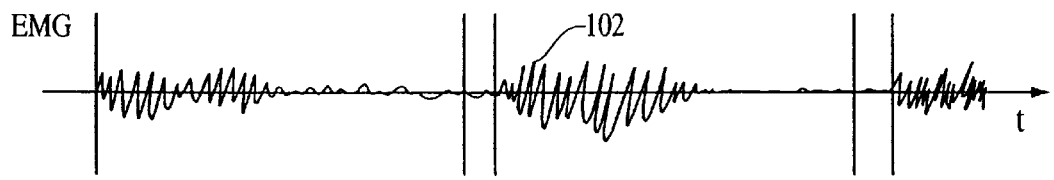
FIG. 5C is a waveform illustrating the EMG activity of the phrenic nerve.
Figure 5D:
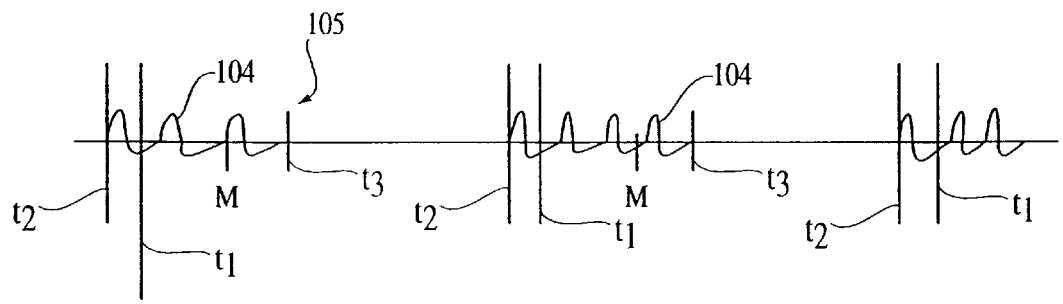
FIG. 5D is a waveform showing the application of stimulation energy to the patient according to the principles of the present invention.

The details of when stimulation commences and terminates according to the present invention are discussed below with reference to FIGS. 5A–5D. FIG. 5A is a waveform illustrating a flow signal 98 of a patient breathing normally, i.e., without any perceptible breathing disorder. Typically, flow signal 98 is output by an airflow meter, such as a pneumatach or thermister device, as discussed above. FIG. 5B is a waveform illustrating a respiratory effort 100 of the patient producing flow signal 98 of FIG. 5A. FIG. 5C is a waveform illustrating the EMG activity 102 of the phrenic nerve (diaphragm). FIG. 5D illustrates the stimulation pulses provided to the patient according to an exemplary embodiment of the present invention.

Conventional stimulation systems that trigger at the onset of inspiration, time $t_1$, attempt to synchronize the opening or the maintenance of the patency of the airway with the action of the diaphragm, which is illustrated in FIG. 5C, so that stimulation is provided as inspiration commences and continues during the inspiratory period Insp. The present invention, on the other hand, applies electrical stimulation energy 104 to the patient, as shown, for example, in FIG. 5D, prior to the onset of inspiration.

One reason for providing stimulation before to the start of inspiration postulated by the present inventors is to counteract the collapsing forces that act on the upper airway. For example, once inspiration commences, a negative pressure is developed in the airway. This negative pressure tends to cause the airway to collapse or reduce in cross sectional area. It is believed that if stimulation is provided after the negative pressure has induced collapse, a greater level of stimulation energy will be needed to overcome the collapsing forces than if stimulation is provided prior to collapse.

In addition, the present inventors postulate that in order to prevent airway collapse in the first place, it is preferable to make the cross-sectional area of the airway as large as possible before inspiratory flow begins in the airway. It can be appreciated that a reduction in the cross-sectional area of the airway increases the resistance to inspiratory flow, which, in turn, increases the negative pressure in the airway that urges the airway to collapse. If stimulation is applied prior to inspiration, the airway is prevented from reducing in cross-sectional area to thereby minimize the resistance to air flow. Minimizing the resistance to airflow improves airflow, thereby reducing negative pressure that potentially causes the airway to collapse. For these reasons, the present invention induces contraction in the muscular associated with the upper airway before a collapsing force, such as the negative pressure developed during inspiration, has the opportunity to cause the airway to collapse.

The present inventors also discovered that in some patients, once a collapse or reduction in the airway has taken place, it is relatively difficult to open the airway by inducing contraction in the upper airway muscles. Although it is not clear why this is the case, the present inventors suggest that once collapse has occurred, the amount of tissue mass that must be moved is prohibitively large. Also, the action of the respiratory muscles in attempting to continue respiration may cause a vacuum to be created that tends to urge the airway tissues together, thereby making it especially difficult for an electrically induced contraction to be effective in opening the airway. Furthermore, the mucus-like characteristics of airway may cause a sealing effect, that also makes it especially difficult for an electrically induced contraction to be effective in opening the airway.

A preferred embodiment of the present invention provides stimulation to the target muscles at time $t_2$, which is between 100 ms and 200 ms prior to the onset of inspiration. This time period is selected as a balance between (1) the need to commence stimulation at a time sufficiently prior to the onset of inspiration to achieve the above functions while (2) minimizing muscle fatigue as a result of the stimulation. Thus, the present invention contemplates providing electrical stimulation at a time prior to inspiration that achieves these functions and is not intended to be limited to the 100 ms–200 ms window noted above.

Causing the stimulation energy to be provided prior to inspiration and, preferably, within the 100 ms and 200 ms time frame, can be accomplished in a variety of ways. For example, flow signal 98 and/or effort signal 100 can be used to determine when the patient is at an appropriate trigger point in the expiratory phase. In an exemplary embodiment of the present invention, the control system determines when flow signal 98 approaches 0 at the end of the expiratory period and causes the electrical stimulation to commence when a distance x of airflow signal 98 from zero at the end of the expiratory period corresponds to time $t_2$. A suitable method for determining when flow signal 98 is at a point corresponding to $t_2$ includes comparing the inhale volume to the exhale volume and triggering when the exhale volume is an appropriate percentage of the inhale volume. It is also possible to compare the inhale time duration to the exhale time duration and trigger when the exhale time duration is an appropriate percentage of the inhale time duration.

Similarly, another embodiment of the present invention determines when time $t_2$ is reached based on effort signal 100 of FIG. 5B. For example, the control system of the present invention can determine, using a variety of techniques, when effort signal 100 is a distance y from a point corresponding to time $t_1$ and cause the electrical stimulation to commence at a time corresponding to time $t_2$. Suitable exemplary methods for determining when effort signal 100 is at a point y corresponding to $t_2$ include triggering when signal 100 reaches a threshold value corresponding to point $t_2$, trigging a fixed time period after the slope of signal 100 becomes negative or after some other reference point, such as a peak, zero crossing or minimum or triggering after a fixed duration of the respiratory cycle. The present invention further contemplates adjusting the trigger point using a multiplying factor to control the target point or threshold.

The length of time that stimulation energy is provided to the patient should be long enough so that the stimulation energy recruits a sufficient amount of muscle fiber to cause the targeted muscle to contract while minimizing muscle fatigue as a result of the stimulation. It is also preferable that the muscle be maintained in a contracted state during the portion of the inspiratory period where airway collapse is most likely to take place. For example, a presently preferred embodiment of the present invention contemplates continuing to provide stimulation during a major portion of the inspiratory phase of the breathing cycle, i.e., for more than half of the inspiratory period Insp. This is accomplished, for example, based on the elapse of time following the application of stimulation so that stimulation stops at time $t_3$, which is at or after a midpoint M of the inspiratory cycle. It is to be understood, however, that the present invention contemplates triggering the cessation of stimulation based on the respiratory characteristics of the patient, using, for example, flow and/or effort signal 98 and 100, so long as stimulation is applied to the patient for a period of time that is long enough to maintain airway patency during the critical portion of the inspiratory period but not so long that muscle fatigue results.

Furthermore, the present invention provides the stimulation energy to the patient at a level sufficient to induce muscle contraction, but not sufficient to cause the patient pain. This is accomplished, for example, by controlling the duty ratio, frequency and amplitude of the stimulation pulses provided by the system during each stimulation interval 105. The physical characteristics of the patient, such as the ability of the muscles to contract and pain tolerance, which are patient dependent, are controlling conditions in determining an appropriate stimulation energy to provide to a patient.

By controlling the onset of stimulation to (1) begin during at a time that satisfies the above functions and (2) continues through at least a portion of the inspiratory phase, (3) at a level that induces muscle contraction but does not cause pain, and (4) in an anterior-to-posterior or posterior-to-anterior direction sublingually in the patient mouth, the present invention is believed to provide optimal stimulation results. The present invention further contemplates that one or more of the electrodes need not be disposed posterior to the frenulum, as discussed above, so long as the above-described four-part stimulation technique is followed.

The present invention also contemplates stimulating the patient upon detecting the occurrence of a breathing disorder. Stimulation based on the occurrence of a breathing disorder can be performed in place of or in addition to the respiration based stimulation method described above. Stimulating based on the occurrence of a breathing disorder, when used in conjunction with above respiration based stimulation timing technique, provides a safety feature in that if the patient experiences an apnea or snoring, even in the presence of the above-described respiration based stimulation timing technique, stimulation can be provided to break or minimize the apnea or snoring. Of course, in order for the present invention to perform stimulation based on the occurrence of a breathing disorder, control unit 50, for example, must be configured to detect the breathing disorder, which can be accomplished using any suitable paradigm, to initiate the stimulation upon detecting the breathing disorder, and to cease stimulation once the disorder is reduced below a predetermined threshold or ceases. If necessary, additional sensors, such as microphone or pressure transducer, can be provided to detect the breathing disorder.

The present invention further contemplates controlling the application, changes in intensity, and cessation of stimulation based on other criteria. For example, the present invention contemplates delaying the application of stimulation energy to the patient after the electromuscular stimulation system has been activated, so that the patient has the opportunity to fall asleep prior to the start of the stimulation therapy. This can be accomplished, for example, by causing a timer to be activated, either manually or automatically upon activation of the stimulation system, and once the time counts out a predetermined time interval, initiating the stimulation therapy. This therapy delay feature can also be based on a conventional clock so that the user can set the therapy to begin at any preselected time during the night. Similarly, the electromuscular stimulation system of the present invention can cease application of the stimulation after the passage of a selectable time period so that stimulation ceases before the patient typically awakes, thereby preventing the user from being awaken by the stimulation therapy. This delay in turning off the stimulation therapy can be based on a time interval or based on a conventional clock.

The present invention also contemplates controlling the stimulation energy applied to the patient in a variety of ways to maximize patient comfort. For example, one embodiment of the present invention contemplates incrementally increasing the intensity of the stimulation energy being delivered to the patient following the actuation of the stimulation system. Typically, this incremental increase in stimulation energy takes place over a number of minutes to allow the patient time to fall asleep without a significant stimulation energy being delivered. The incremental increase can be linear or can take place in discrete steps. Furthermore, this increase can take place in place of or after the delay period discussed above and is analogous to the ramp feature found in conventional pressure support devices, e.g., CPAP, devices.

Another embodiment of the present invention contemplates incrementally decreasing the intensity of the stimulation energy being delivered to the patient. This decrease can take place in place of or before the delay in turning off the stimulation therapy discussed above. The intensity of the stimulation can also be controlled based on the patient's sleep stages, assuming, of course, that the appropriate sensors and control systems are provided to detect and classify the patient's sleep stages.

The present invention further contemplates providing various methods for interrupting the stimulation therapy. For example, a pause function that stops stimulation therapy can be initiated by manually actuating an input device, such as a button, on the control unit or by actuating a remote input device. The stimulation therapy can also be interrupted automatically, if, for example, a malfunction is detected or if the patient removes the dental device from their mouth. Restart of the stimulation therapy can begin automatically, after the elapse of a fixed or selectable time period or once the dental device is reinserted into the mouth, for example, or by manually actuating the input device, i.e., actuating an input button or a remote control. Restart of the stimulation therapy can begin at the stimulation energy levels existing prior to the pause, at the initial energy level, or at some other preselected level. In addition, the stimulation therapy delay function and/or the incremental intensity variation function can be instituted during the restart so that the user again has the opportunity to fall asleep in the absence of any stimulation therapy or in the absence of significant stimulation.

The present invention also contemplates providing a safety feature in which a maximum stimulation energy that can be provided to the patient is set. This can be accomplished via control unit 50. This stimulation energy provided to the patient will not exceed the set maximum regardless of the stimulation energy set by the user on the control unit. It is preferable that the means by which the maximum stimulation energy is set is not readily accessible so that it cannot be altered inadvertently or tampered with by the user. The use of a password that must be input in order to alter the maximum setting is an example of such a security/safety feature.

In still another embodiment of the present invention, the electromuscular stimulation system is provided with an automatic turn-on and/or an automatic turn-off feature. This provides the advantages of simplifying the operation of the system and conserving power, for example. Sensors on the dental appliance, such as a temperature sensor or galvanic type sensor can detect when the appliance is inserted into the patient's mouth. The output of these sensors are used to control the actuation and deactivation of the stimulation system of the application and cessation of the stimulation therapy.

With the growing popularity of managed healthcare, healthcare providers are becoming more concerned that the patients actually use the prescribed therapy devices. To meet this concern, the present invention monitors patient compliance by storing information regarding the use of the electromuscular stimulator, such as the amount of time that the unit was turned on or that the dental appliance was in contact with the patient and/or the amount of time that stimulation energy was provided to the patient.

In one embodiment discussed above, stimulation energy is provided once an apneic event is detected. In another embodiment, stimulation energy is provided in synchronization with the patient's respiratory cycle. These, features of the present invention provide a relatively reliable and accurate indication of the actual usage of the electromuscular stimulator.

Furthermore, because the electromuscular stimulator is capable of communicating with external devices using a modem, for example, patient compliance can be remotely monitored by the healthcare provider with little or no patient involvement. This same remote patient compliance monitoring feature also permits the healthcare provider to monitor and/or control the operating status of the stimulator, for example, by causing the device to run a diagnostic routine and reports the results of that routine or change the operating setting of the device.

Figure 6:
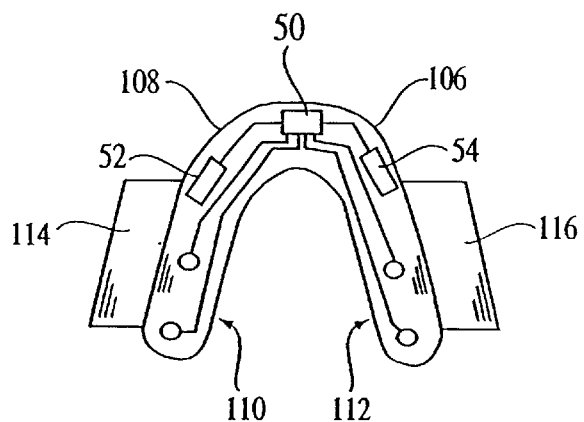
FIG. 6 is a schematic diagram of an electromuscular stimulating system according to a second embodiment of the present invention.

One embodiment of the present invention contemplates that each component of electromuscular stimulation system 30 illustrated in FIG. 3 is separate and isolated from the other components. For example, control unit 50 is provided in a housing that sits at the patient's bedside, power supply 52 is the AC power available from a conventional outlet, respiration sensor 54 is a device externally attached the patient at a first location, and dental appliance 32 is inserted in the patient's mouth. It is to be understood, however, that each component need not be physically separated from the other components. On the contrary, depending on the type, the sensor may be provided on the dental application and/or the power supply may be included in the control unit. In another embodiment of the present invention, all of the components are provided on the dental appliance and contained in the patient's mouth during normal operation. FIG. 6 illustrates such an embodiment.

As shown in FIG. 6, dental appliance 106 includes a support member 108 that carries control unit 50, power supply 52, respiration sensor 54, and two groups 110 and 112 of electrodes, one group located on each lateral arm. Each group of electrodes, unlike the groups of electrodes illustrated in the previous figures, contains only two electrodes. However, as in the previous embodiment, the electrodes in groups 110 and 112 are disposed on the support member such that one electrode is posterior to the other electrode when the dental appliance is properly inserted in the patient's mouth.

Other than being miniaturized to fit on or within the support member and, hence, in the patient's mouth, control unit 50, power supply 52, and respiration sensor 54 are identical to those discussed above. It is to be understood, however, some of the components or sub-assemblies of one or more components of the electromuscular stimulating system may be provided at locations other than on or in the dental appliance. For example, depending on the type of respiration sensor used, the present invention contemplates that the respiration sensor be located at positions on or in the patient other than within the mouth. More specifically, a belt or sensor that measures the displacement of the chest may be provided at or around the patient's thorax and communicates, either using wires or wirelessly, with the control unit and/or a receiver provided on the dental appliance. Finally, the dental appliance of FIG. 6 includes a pair of attaching members 114 and 116 for securing the dental appliance within the mouth. The attaching members illustrated in FIG. 6, unlike the wire-like devices in FIG. 1, are moldable, relatively rigid flaps that can be customized to match the patient's teeth.

The present invention further contemplates that each component in the electromuscular stimulating system communicates, as shown in FIG. 3 or FIG. 6, via hardwires, or, if appropriate, wirelessly. For example, sensor 54 can wirelessly communicate with control unit 50 or with a receiver or transceiver coupled to the control unit. The present invention also contemplates, for example, providing the power supply on the dental appliance and remotely controlling the application of stimulation energy from the power supply to the electrodes via the control unit, which is not mounted on the dental appliance. This embodiment, like that of FIG. 6, is particularly advantageous in that there are no wires passing into the patient's mouth.

Figure 7:
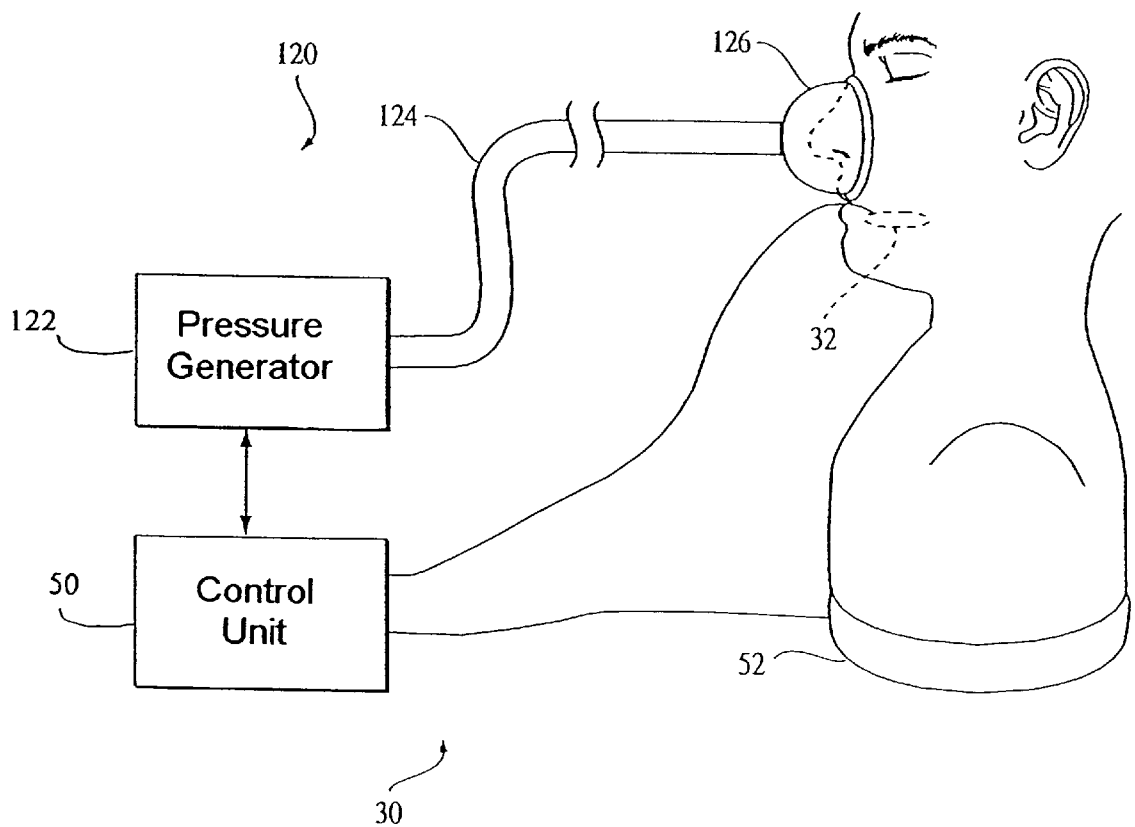
FIG. 7 is a schematic diagram of an electromuscular stimulating system according to a third embodiment of the present invention that includes a pressure support device.

In the previous embodiments of the present invention, the electromuscular stimulating system is the sole means for treating the patient's breathing disorder. It is to be understood, however, that the present invention contemplates using the electromuscular stimulating system in conjunction with other techniques for treating breathing disorders. For example, FIG. 7. illustrates the use of electromuscular stimulating system 30 with a pressure support system 120 that applies positive air pressure at the mouth and/or nose of the patient to "splint" the airway. It is believed that the electromuscular stimulation will reduce the pressures necessary to be provided by the pressure support system 120 in order to splint the airway and treat the breathing disorder. It is well recognized that the pressure needed to be provided to the patient by the pressure support device to treat the breathing disorder should be kept as low as possible.

The present invention contemplates that the electromuscular stimulating system 30 of the present invention can be used in conjunction with most, if not all, conventional pressure support systems. Such pressure support systems typically include a pressure generator 122 that generates a gas flow, a conduit 124 that carries the gas flow to the patient, and a patient interface device 126 that communicates the conduit with the patient's airway. Examples of pressure support devices that are used in conventional pressure support systems include a CPAP (continuous positive airway pressure) device, bi-level devices, which provide variable levels of pressure support during the patient's respiratory cycle, such as the Respironics BiPAP® devices, PAV® devices and PPAP devices. Examples of suitable patient interface devices include nasal masks, oral appliances, nasal/oral masks, full face masks, hoods, nasal cannulas, trachea tube, and any other device that communications a gas flow with the patient's airway.

Figure 8A:
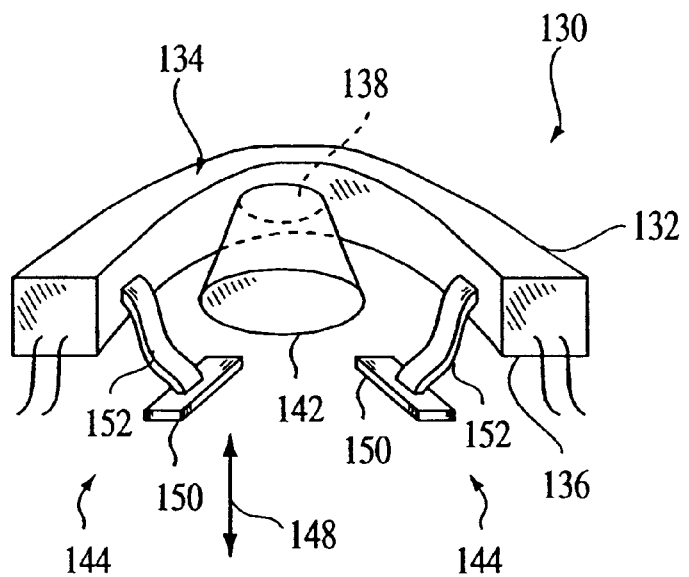
FIG. 8A is a rear perspective view and FIG. 8B is a bottom view of a dental appliance that provides electromuscular stimulation and oral positive airway pressure according to the principles of the present invention.
Figure 8B:
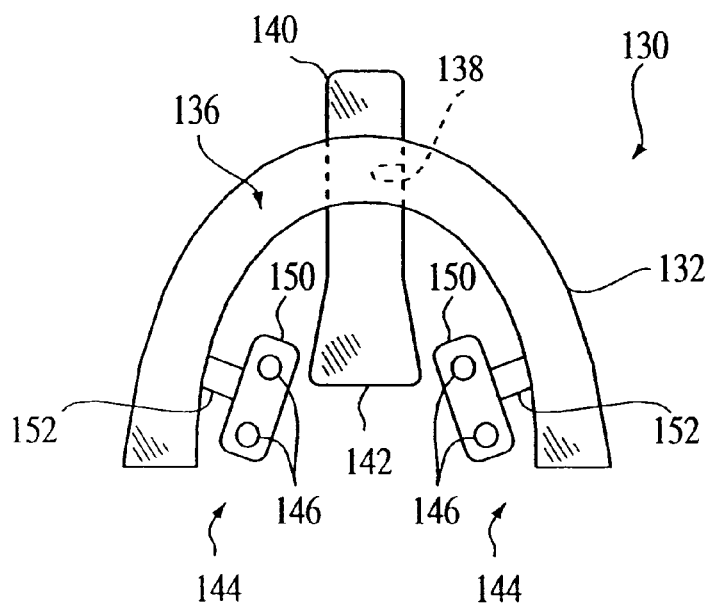

The present invention also contemplates providing the electromuscular stimulation in addition with other medical treatments. For example, FIGS. 8A and 8B illustrate an intraoral dental appliance 130 that provides electromuscular stimulation and oral positive airway pressure to a patient according to the principles of the present invention. Dental appliance 130 includes a mouthpiece 132 that attaches to the patient's teeth. In a preferred embodiment of the present invention a superior surface 134 of mouthpiece 132 attaches to the upper teeth and an inferior surface 136 attaches to the lower teeth. In addition, surfaces 134 and 136 are preferably moldable or customizable to correspond to the dental pattern of the patient.

Mouthpiece 132 includes an orifice 138 passing therethrough to provide a channel for passing a breathing gas, such as air, from an external breathing gas source to the airway of the patient. The external breathing gas source can be any suitable pressure support device, such as the pressure support devices discussed above or a pressurized container of gas. In the illustrated embodiment, a connector 140 is coupled to one end of the orifice and a flexible tube 142 is coupled to the other end. Connector 140 provides a connection for attaching dental appliance 130 to a breathing circuit (not shown). Flexible tube 142 is configured so as to overly the patient's tongue when the dental appliance is properly positioned with the patient's oral cavity. Flexible tube 142 directs the breathing gas provided by the external source over the patient's tongue to the airway to, among other things, minimize drying of the tongue and provide the pressurized gas as directly as possible to the patient's airway. The present invention contemplates that the length, configuration, and materials for connector 140 and flexible tube 142 can vary so long as the above objects are achieved.

Dental appliance 130 also includes a pair of electrode support structures 144 coupled to mouthpiece 132 for supporting electrodes 146. The present invention contemplates that support structures 144 can have a variety of configurations so long as the support functions discussed above are achieved. Namely, electrodes 146 should be moveable in a direction indicated by arrow 148 (perpendicular to surfaces 134 and 136) and not substantially moveable in other directions, i.e., laterally or in a front-to-back direction, so that the electrodes are held against the floor of the mouth posterior to the frenulum during use.

In the illustrated embodiment, each electrode support structure 144 includes a substrate 150 attached to mouthpiece 132 via a support arm 152. Electrodes 146 are disposed on the inferior side of substrate 150. It is to be understood, however, that substrate 150 can be eliminated so that the electrodes are attached directly to the mouthpiece using one or more support arms. However, substrate 150 is beneficial in that it serves as an insulator to ensure that electrical stimulation is provided only to those locations where desired. It is to be understood that the present invention contemplates that substrate 150 and support arm 152 can have a variety of configurations or include one or more components. In addition, the attachment point and means for attaching the various components of the electrode support structure can be any suitable point or attaching mechanism so long as the functions of the support structures are provided.

Figure 9A:
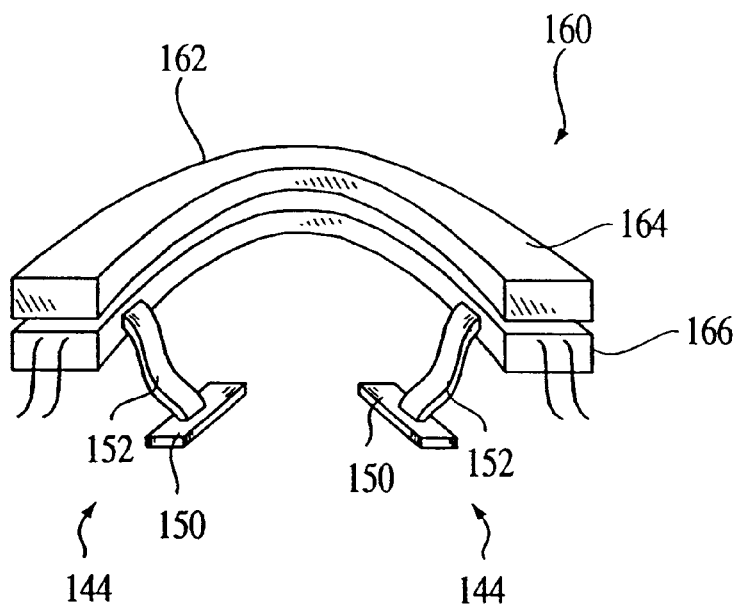
FIG. 9A is a rear perspective view.
Figure 9B:
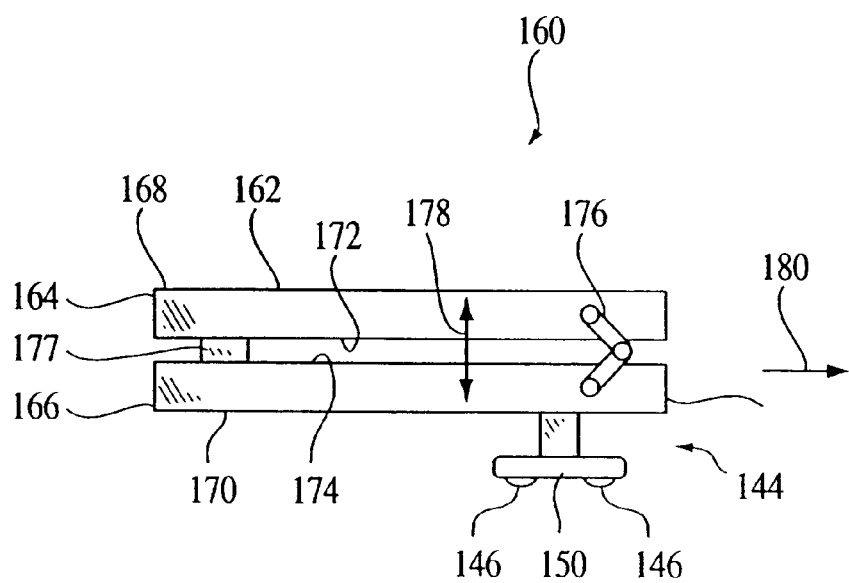
FIG. 9B is a side view of a dental appliance that provides electromuscular stimulation and mandibular positioning according to the principles of the present invention.

FIGS. 9–9B illustrate other variations in which the electrical stimulation techniques are used in conjunction with breathing disorder treatment. More specifically, FIG. 9A–9B illustrate an intraoral dental appliance 160 and 160' that provides electromuscular stimulation according to the principles of the present invention and mandibular position control.

The partial or complete, intermittent airway obstruction that occurs during sleep in some OSA sufferers is caused or exacerbated by anterior movement of the lower jaw, referred to as the mandible, during sleep. To prevent mandibular movement that may adversely affect the airway opening, it is known to provide a mandibular positioning dental appliance to control the position of the jaw. A further embodiment of the present invention incorporates the electromuscular stimulation system into a mandibular positioning appliance.

FIGS. 9A and 9B are rear perspective and side views of an exemplary embodiment of a dental appliance 160 that includes the mandibular positioning function discussed above and the electromuscular stimulation function according to the principles of the present invention. Mandibular positioning dental appliance 160 includes a mouthpiece 162 that attaches to the patient's upper and lower teeth. Mouthpiece 162 includes two components, an upper member 164 that attaches to the patient's upper teeth or bone structure and a lower member 166 that attaches to the teeth or jaw. More specifically, a superior surface 168 of upper member 164 attaches to the upper teeth and an inferior surface 170 of lower member 166 attaches to the lower teeth. Surfaces 168 and 170 are preferably moldable or customizable to correspond to the dental pattern of the patient so that the upper and lower members securely attach to the patient. An inferior surface 172 of upper member 164 generally faces a superior surface 174 of lower member 196. A mechanical linkage 176 couples upper member 164 and lower member 166 to one another and controls or limits the movement of one member relative to the other at least in certain directions. In a preferred embodiment of the present invention, at least one spacer 177 is provided at the anterior portion of the mouthpiece and attached to the upper member or lower member to maintain a comfortable spacing between these members. It is to be understood that one or more spacers can be provided at other locations within the mouthpiece and that the spacer or spacers can be formed integrally with the mouthpiece member.

In a preferred embodiment of the present invention, linkage 176, which is preferably provided on both lateral arms of the mouthpiece for stability, permits at least limited movement of lower member 166 relative to upper member 164 in a direction indicated arrows 178. However, linkage 176 limits movement of lower member 166 relative to upper member 164 in a direction 180 to a certain predetermined range so that the patient's jaw, which is attached to lower member 166, does not move posteriorly relative to the upper member more than a predetermined amount. The predetermined amount is an amount which, if exceeded, tends to result in a reduction or blockage of the airway. Thus, the mandibular positioning feature allows for movement of the lower member relative to the upper member but permits only limited movement of the lower member in the direction of arrow 180 relative to the upper member to prevent the patient's jaw from moving posteriorly relative to the upper teeth to a degree that might result in airway collapse or reduction.

While control of the movement of the lower member relative to the upper member is provided in the illustrated embodiment via a mechanical linkage, it is to be understood that the present invention is not limited to this example of a position control mechanism. For example, the present invention contemplates that the upper member and the lower member can be fixed to one another, as in the embodiment illustrated in FIGS. 8A and 8B, for example. If desired, the upper and lower members can be fixed to one another in an offsetting relation to provide a desired mandibular positioning. In these embodiments, an airway, such as orifice 138, can be provided to allow the patient to breath through the mouth. Of course, if the patient breaths through the nose, such an orifice is not needed.

As in the embodiment illustrated in FIGS. 8A and 8B, dental appliance 60 includes a pair of electrode support structures 144 and 144' coupled to mouthpiece 162 for supporting electrodes 146. The configuration for the support structures and/or the electrodes, the placement location of the support structures on the mouthpiece and attachment mechanism, the functions and the support structures and alternative configurations are the same as those discussed above with respect to FIGS. 8A and 8B. Therefore, detailed descriptions of these embodiments and modifications are omitted from the present discussion of FIGS. 9A and 9B for simplicity.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. An electromuscular stimulation device comprising,
   a first member adapted to engage a structure associated with a patient's upper dentition;
   a second member adapted to engage a structure associated with a patient's mandible;
   a first electrode supported by the second member in a sublingual position posterior to a frenulum and generally proximate to one of a first molar, a second molar and a third molar of the patient;
   a second electrode supported by the second member in a sublingual position posterior relative to the first electrode; and
   a connecting assembly connecting the first member and the second member so as to limit movement of the first member relative to the second member, thereby controlling a position of the patient's mandible relative to the upper dentition during use of the electromuscular stimulation device.

2. The device of claim 1, wherein the first member is adapted to engage the patient's upper teeth, and wherein the second member is adapted to engage the patient's lower teeth.

3. The device of claim 1, wherein the first electrode and the second electrode are supported by the second member such that the first electrode and the second electrode are disposed on a same side of a patient's oral cavity.

4. The device of claim 1, wherein the connecting assembly is a mechanical linkage between the first member and the second member.

5. The device of claim 1, wherein the connecting assembly is defined by fixing the first member and the second member in an engaged relation.

6. The device of claim 1, further comprising a passageway defined between the first member and the second member that is adapted to communicate an airway of the patient with a supply of breathing gas.

7. The device of claim 1, further comprising a common support member supporting the first electrode and the second electrode, and wherein the common support member is operatively coupled to the second member.

8. An electromuscular stimulating system comprising:
   (1) an intraoral dental appliance, comprising:
       a first member adapted to engage a structure associated with a patient's upper dentition,
       a second member adapted to engage a structure associated with the patient's mandible,
       a first electrode supported by the second member in a sublingual position posterior to a frenulum and generally proximate to one of a first molar, a second molar and a third molar off the patient,
       a second electrode supported by the second member in a sublingual position posterior relative to the first electrode, and
       a connecting assembly connecting the first member and the second member so as to limit movement of the first member relative to the second member.
       thereby controlling a position of the patient's mandible relative to the upper dentition
       during use of the intraoral dental appliance; and
   (2) a stimulation unit operatively coupled to the first electrode and the second electrode to provide stimulating energy to a portion of the patient via the first and the second electrodes such that current flow of the stimulating energy takes place in an anterior-to-posterior direction or a posterior-to-anterior direction.

9. The system of claim 8, wherein the first electrode and the second electrode are supported by the second member such that the first electrode and the second electrode are disposed on a same side of a patient's oral cavity.

10. The system of claim 8, wherein the connecting assembly is a mechanical linkage between the first member and the second member.

11. The system of claim 8, wherein the connecting assembly is defined by fixing the first member and the second member in an engaged relation.

12. The system of claim 8, further comprising a supply of breathing gas and a passageway defined between the first member and the second member that communicates an airway of the patient with said supply of breathing gas.

13. The system of claim 8, further comprising a sensor adapted to detect a physiological characteristic of the patient and to provide a signal to the stimulation unit indicative of the physiological characteristic, and wherein the stimulation unit controls the energy provided to the first and the second electrodes based on the signal from the sensor.

14. The system of claim 13, wherein said supply of breathing gas comprises a pressure generator and a conduit having a first end operatively coupled to the pressure generator and a second end operative coupled to the passageway.

* * * * *